United States Patent [19]

Zabotto et al.

[11] Patent Number: 4,661,343

[45] Date of Patent: Apr. 28, 1987

[54] AQUEOUS OR ANHYDROUS COSMETIC PREPARATION CONTAINING A FATTY PHASE CONSISTING ESSENTIALLY OF KARITE OIL

[75] Inventors: Arlette Zabotto, Paris; Jacqueline Griat, Ablon, both of France; Umberto Bracco, La Tour de Peilz, Sweden

[73] Assignee: Societe Anonyme dite: L'Oreal, Paris, France

[21] Appl. No.: 679,942

[22] Filed: Dec. 10, 1984

[30] Foreign Application Priority Data

Dec. 12, 1983 [LU] Luxembourg ............................ 85130

[51] Int. Cl.$^4$ ...................... A61K 7/02; A61K 7/021; A61K 7/42; A61K 7/44
[52] U.S. Cl. ............................... 424/59; 424/DIG. 5; 424/60; 424/63; 514/844; 514/845; 514/846; 514/847; 514/937; 514/938; 514/969
[58] Field of Search .......................................... 424/59

[56] References Cited

U.S. PATENT DOCUMENTS 3,911,105  10/1975  Papantoniou et al. ................. 424/59
4,466,955  8/1984  Calvo et al. ............................ 424/59

FOREIGN PATENT DOCUMENTS 1269621  7/1961  France ................................. 424/64
5087714  7/1980  Japan ................................... 424/59
2102290  2/1983  United Kingdom ................. 424/64

OTHER PUBLICATIONS

Derwent Abstract, 57893C/33-Abstract of Japanese Patent cited above.
Mital, Drug & Cosmetic Industry, 5/1977, pp. 30 to 32.

*Primary Examiner*—Dale R. Ore
*Attorney, Agent, or Firm*—Cushman, Darby & Cushman

[57] ABSTRACT

A cosmetic preparation contains, as a fatty phase, karite oil having the following characteristics: palmitic acid ($C_{16}$), 3–5 percent; stearic acid ($C_{18}$), 22–30 percent; oleic acid ($C_{18:1}$), 55–65 percent; linoleic acid ($C_{18:2}$), 0.5–1.5 percent; and arachidic acid ($C_{20}$), 0.5–1.5 percent, said percentages being based on the total weight of fatty acid present in said karite oil, a viscosity of 100–300 centipoises, a melting point of 5.1°–5.4° C., a crystallization temperature of 2.9°–3° C. and an unsaponifiable content of 1.2–1.5 percent.

10 Claims, No Drawings

AQUEOUS OR ANHYDROUS COSMETIC PREPARATION CONTAINING A FATTY PHASE CONSISTING ESSENTIALLY OF KARITE OIL

The purpose of this invention is to obtain new aqueous or anhydrous cosmetic preparations whose fatty phase is essentially based on a vegetable oil hereafter referred to as "karite oil", possibly mixed with other oils, fats or waxes.

Most cosmetic preparations contain, in varying levels of concentration, a fatty phase generally consisting of a mixture of at least an oil, a fat and/or a wax. This is particularly true of oil-in-water or water-in-oil emulsions, gels, oils for face and body care, milks and make-up products such as rouge or lipstick.

Oils form a large part of these fatty phases and can be selected from a wide range of either natural or synthetic products.

Due to their properties, natural oils are generally preferred, in particular vegetable oils, but their characteristics are not always constant, depending on the place of origin of the oils, the treatments to which they were subjected, and their generally high cost.

As an example, jojoba oil, whose excellent cosmetic properties have been acknowledged by various specialists and which is widely used in many cosmetic preparations, is an oil relatively expensive, on the world market, and its physical characteristics are not always constant, depending on its origin and the extraction process adopted. This influences not only the cost of production but also the capability of reproducing exactly the preparations that contain it.

Following much research, it has just been noted that it was possible to obtain excellent cosmetic preparations containing a fatty phase by using karite oil, i.e. karite olein, derived from karite butter, that oil having never been yet recommended as the fat element in the fatty phase of a cosmetic preparation, to the knowledge of the Company applying for this patent.

Although the characteristics of that oil differ from those of jojoba oil, it does impart very similar properties to cosmetic preparations, notably through its protecting and softening effect on skin.

It was also noted that associating that oil with at least one essential fatty acid or their mixtures, in particular with Vitamin F, made it quite resistant to oxidation.

In other respects, karite oil proved to have considerable protective power against erythema caused by ultraviolet rays (UVB).

The object of this invention is a new industrial product consisting of an either aqueous or anhydrous cosmetic preparation, whose fatty phase is essentially karite oil or a mixture of karite oil and at least one other oil, fat and/or wax.

Karite oil comes from the extraction of karite butter by an organic solvent.

Karite butter itself comes from the fruit (almonds) of the tree (Butyrospermum Parkii) found in Mali, Sudan, Senegal and Gabon. The almond contains from 45 to 55% fat which is extracted and refined.

Karite butter is in the form of a yellow product with the following characteristics:

Palmitic acid ($C_{16}$): 5–7%
Stearic acid ($C_{18}$): 40–44%
Oleic acid ($C_{18:1}$): 48–51%
Linoleic acid ($C_{18:2}$): 2–5%
Arachidic acid ($C_{20}$): 0–0.5%

(these percentages being expressed as compared to the total weight of fatty acids)

Specific gravity at 15° C.: 0.915–0.918
Index of refraction at 40° C.: 1,4633–1,4668
Iodine index: 51–60
Index of saponification: 170–185
Melting-point: 37°–38° C.

Two fractions may be obtained from karite butter, one called solid or "karite butter stearin" known as a cocoa butter substitute in chocolate and candy making, the other called liquid or "karite butter oil".

The liquid fraction results from the continuous and/or discontinuous fractionating of karite butter by organic solvent, such as alkane, ketone, alcohol or their azeotropic binary and tertiary mixtures.

Extraction is performed preferably with acetone at temperatures between 12° and 20° C., this depending upon the ratio of karite butter to the organic solvent used. After filtration in cold state, the solid fraction or stearin is separated and the solvent phase is evaporated, resulting in karite oil which represents ⅓ by weight of the karite butter subject to fractionation.

The karite oil obtained in this fashion has the following characteristics:

Palmitic acid ($C_{16}$): 3–5%
Stearic acid ($C_{18}$): 22–30%
Oleic acid ($C_{18:1}$): 55–65%
Linoleic acid ($C_{18:2}$): 0.5–1.5%
Arachidic acid ($C_{20}$): 0.5–1.5%

(These percentages being expressed as compared to the total of fatty acids)

Viscosity: 100–300 centipoises.
Melting-point: 5.1°–5.4° C.
Crystallization: 2.9°–3° C.
Unsaponifiable: 1.2–1.5%
Unsaponifiable composition (by % of the total unsaponifiable):
Alkanes: 15–18%
Long-chain alcohols: 10–12%
Sterols: 60–66%
Triterpenic alcohols: 10–15%

The sterols in the unsaponifiable are essentially the following:

Campesterol: 10±2%
Stigmasterol: 5±1%
$\beta$ sitosterol: 52±4%
$\Delta 5$ Avenasterol: 15±2%
$\Delta 7$ Avenasterol: 10±1%

(These percentages being expressed as compared to total sterols)

The triterpenic alcohols in the unsaponifiable, expressed in % of the total triperpenic alcohols, are as follows:

Cycloartanol: 2%
$\alpha$ Amyrin: 46±2%
$\beta$ Amyrin: 10±1%
Butyrospermol: 26±1%
Cycloartenol: 2%
Lupeol: 16+1%
24-methylene Cycloartenol: traces.

Karité oil should have preferably the following fatty acids ratios:

$$[(C_{16}+C_{18})/C_{18:1}] = 0.518 \pm 0.01$$

$$(C_{16}/C_{18:1}) = 0.064 \pm 0.003$$

EXAMPLE OF KARITE OIL PREPARATION 1000 g of karite butter are dissolved at 40° C. in 7,000 ml of acetone, followed by cooling of the mixture at 15° C., Six hours later, the mixture is cold-filtered to obtain the solid fraction which is separated and the solvent phase containing the liquid fraction of karite. The solvent, which is recycled, is evaporated by distillation and approximately 300 g of the liquid fraction of karite oil are obtained.

The karite oil obtained in this manner has the following characteristics:
Palmitic acid ($C_{16}$): 3.8±0.18
Stearic acid ($C_{18}$): 26.8±0.12
Oleic acid ($C_{18:1}$): 59.0±0.23
Linoleic acid ($C_{18:2}$): 0.9±0.18
Arachidic acid ($C_{20}$): 0.8±0.1
Viscosity: 170 centipoises.
Melting-point: 5.3° C.
Crystallization: 2.95° C.

According to this invention process, karite oil is present with a concentration of approximately 1 to 80% by weight as compared to the total weight of the cosmetic preparation, such concentration being preferably 2 to 30% by weight in the case of an emulsion and able to reach up to approximately 80% in the case of an anhydrous ointment.

The other components of the fatty phase are either vegetable or animal oils or mineral oils, or still, synthetic oils.

In other respects, the fatty phase may also contain, in some proportion, fats and/or waxes.

Among the vegetable or animal oils, modified or not, the following may be mentioned: sweet almond oil, avocado oil, ricin oil, olive oil, jujube oil, sesame oil, soybean oil, colza oil, perhydrosqualene, calophyllum oil, lanolin and its derivatives.

Among the mineral oils may be mentioned, for example, vaseline oil, and among the synthetic oils, ethyl and isopropyl palmitate, alkyl myristates such as isopropyl, butyl and cetyl myristate, triglycerides of octanoic acid decanoic acids (for example, the product sold under the name "MIGLYOL 812") by DYNAMIT NOBEL Company, cetyl ricinoleate, stearyl octanoate (purcellin oil), hydrogenated polyisobutene and silicon oils soluble in the other oils such as, for example, dimethyl polysiloxane or methylphenyl polysiloxane.

Among the waxes may be mentioned in particular carnauba wax, beeswax, ozokerite, candelilla wax, Montan wax and microcrystalline waxes.

These oils and waxes are commonly utilized in the cosmetics industry and are well known by cosmeticians as being susceptible of forming substances suited to achieving the fatty phases or oils of various cosmetic products.

In addition to the oils and waxes mentioned above, the fatty phase according to the invention may also contain some compounds considered as fatty products, i.e. long-chain alcohols such as cetylic alcohol, stearylic alcohol, myristic alcohol, hydroxystearylic alcohol, oleic alcohol or isostearylic alcohol.

These compounds, when present in the fatty phase, represent generally from 0.5 to 5% of the total weight of the preparation.

The fatty phase may also contain certain polymers such as, for example, vinyl polylaurate.

Generally speaking, the fatty phase is present in the proportion of approximately 4 to 99.9% by weight of the cosmetic preparations total weight.

Cosmetic preparations according to the invention are generally all aqueous or anhydrous preparations containing a fatty phase.

Among these preparations may be mentioned in particular those which appear under the form of fluid emulsions, lotions, or more substantial emulsions.

These preparations are, for example, milks or softening creams, milks or creams for hand care, make-up removing creams or milks, foundation bases, sun-screen milks or creams, artificial tanning milks or creams, milks or creams against perspiration, shaving creams or foams.

In a primary form, cosmetic preparations according to the invention may essentially consist of the fatty phase, taking then the form of a sun-screen oil (containing a sun filter absorbing ultra-violet rays), a hand care oil, a body or hair care oil, a pre-shave or after-shave oil, a bath oil, a gel, an ointment, a stick.

When preparations are in the form of creams or milks, they are more particularly emulsions of the type: water-in-oil or oil-in-water, whose fatty phase represents from 4 to 60% by weight, the water phase from 30 to 90% and the emulsifying agent from 1 to 20%, preferably from 2 to 12%, by weight.

Among emulsifying agents may be mentioned in particular:
Fatty polyoxyethylene or polyglycerol alcohols, oxyethylene or non-oxyethylene alkyl sulfates, mixtures of at least one lanolate, such as magnesium, calcium, lithium, zinc or aluminum lanolate and hydrogenated lanoline and/or lanoline alcohol, esters of fatty acids and of polyols such as glycerol or propylene glycol.
Monoesters of fatty acids and of polyoxyethylene sorbitan, for example the products sold by ATLAS Company under the name "TWEEN".

These preparations may also contain other conventional ingredients, in particular thickening agents or jellifying agents such as, for example:
Magnesium and aluminum silicates.
Ether-vinylic/anhydride maleic copolymers, such as the products sold under the name "VISCOFAS X 100,000" or "VISCOFAS I. 100" by I.C.I. COMPANY, combined with amino-acids.
or Carboxyvinylic polymers such as the products sold under the name "CARBOPOL" by GOODRICH Company.
or still, Gels of organically modified montmorillonite and neutral oil, for example the product "Miglyol gel" sold by DYNAMIT NOBEL Company.

Preparations obtained according to the invention contain other various ingredients, in particular coloring agents, perfumes, preserving agents, UV filters, pigments, pearlizing agents and mineral or organic fillers.

In a preferred form of the invention, karite oil is combined with at least one essential fatty acid or a mixture of those acids, in particular with Vitamin F in the form of free or esterified acid, the combination being quite resistant to oxydation.

The expression "essential fatty acid" means an unsaturated fatty acid having at least two double bonds such as:

(1) linoleic acid or 9,12-octadecadienoic acid and its stereoisomers and in particular the Z-9,Z-12 isomer as well as its position isomers or conjugated linoleic acids, i.e.: 9,11-octadecadienoic acid and its stereoisomers, and 10,12 octadecadienoic acid and its stereoisomers.

(2) αlinolenic acid or 9,12,15-octadecatrienoic acid and its stereoisomers, and in particular the Z-9, Z-12, Z-15 isomer.

(3) γlinolenic acid or 6,9,12-octadecatrienoic acid and its stereoisomers, (4) and arachidonic acid or 5,8,11,14-eicosatetraenoic acid and its stereoisomers.

Vitamin F is essentially made of linoleic acid and its isomers, the 9,12 isomer being present in a proportion varying between approximately 40 and 70%, the total quantity of linoleic acids (linoleic acid + isomers) representing about 80 to 90%, the rest being essentially a mixture of other essential fatty acids.

In this preferred form of applying the invention process, the essential fatty acid, taken alone or in a mixture, is generally present in proportions of 0.2 to 20% by weight as compared to the weight of karite oil.

In order to improve the stability of preparations, these can also contain at least one anti-oxidizing agent such as, for example, butylhydroxyanisole (BHA) or butylhydroxytoluene (BHT) or a mixture of those substances in the proportion of approximately 0.002 to 0.2% as compared to the total weight of the preparation.

As an illustration, several non-restrictive examples of aqueous or anhydrous cosmetic preparations, conforming to the invention, are given below.

EXAMPLE 1

| Care cream in the form of oil-in-water emulsion | |
|---|---|
| Fatty phase: | |
| Cetylic acid | 0.5 |
| Karite oil | 18 |
| Synthetic perhydrosqualene | 4 |
| Glycerol stearate | 2 |
| Tween 60 (sorbitan monostearate at 20 moles of ethylene oxide) | 1 |
| Stearic acid | 1.4 |
| Triethanolamine | 0.7 |
| Carbopol 940 (neutralized by triethanolamine) | 0.4 |
| Vitamin F | 2 |
| Antioxidant (BHA + BHT) | 0.015 |
| Fragrance | 1 |
| Water + preserving agent (methyl parahydroxybenzoate) QSP | 100% by weight |

EXAMPLE 2

| Care cream in the form of water-in-oil emulsion | |
|---|---|
| Fatty phase: | |
| Mycrocrystalline wax | 1 |
| Vaseline oil | 5 |
| Corn germ oil | 2 |
| Karite oil | 12 |
| Esters of fatty acids (C8–C18) and of fatty alcohols (C12–C18) | 1 |
| Sorbitan monoisostearate | 5 |
| Gel of organically modified montmorillonite and neutral oil (triglycerids of caprylic and capric acids | 5 |
| Propylene glycol | 3 |
| BHA + BHT | 0.01 |
| Water + preserving agent QSP | 100% by weight |

EXAMPLE 3

| Care cream in the form of water-in-oil emlusion | |
|---|---|
| Fatty Phase: | |
| Isopropyl myristate | 8 |
| Paraffin oil | 18 |
| Karite oil | 22 |
| Ozokerite | 4 |
| Magnesium lanolate | 14.4 |
| Lanolin alcohol | 3.6 |
| BHA + BHT | 0.01 |
| Water and methyl parahydroxybenzoate QSP | 100% by weight |

EXAMPLE 4

| Make-up removing milk | |
|---|---|
| Fatty phase: | |
| Vaseline oil | 6 |
| Isopropyl palmitate | 5 |
| Karite oil | 6 |
| Glycerol Stearate | 2 |
| Stearic acid | 1.4 |
| Triethanolamine | 0.7 |
| Anhydride maleic copolymer/methyl vinyl reticulated ether (Viscofas × 100,000) | 0.6 |
| Lysine | 0.5 |
| Antioxidant (BHA + BHT) | 0.002 |
| Water + preserving agent QSP | 100% by weight |

EXAMPLE 5

| Make-up removing cream | |
|---|---|
| Fatty phase: | |
| Karite oil | 15 |
| Glycerol stearate | 2 |
| Stearic acid | 1.4 |
| Triethanolamine | 0.7 |
| Carbopol 940 (GOODRICH) | 0.3 |
| Lysine | 0.5 |
| BHA + BHT | 0.015 |
| Water + preserving agent QSP | 100% by weight |

EXAMPLE 6

| Rinsing soap cream | |
|---|---|
| Fatty phase: | |
| Mineral oil | 15 |
| Karite oil | 5 |
| Triethanolamine stearate | 12 |
| Propylene glycol | 10 |
| Viscofas × 100,000 | 0.4 |
| Arginine | 0.35 |
| BHA + BHT | 0.005 |
| Water + preserving agent QSP | 100% by weight |

EXAMPLE 7

| Tinted cream in the form of an oil-in-water emulsion | |
|---|---|
| Fatty phase: | |
| Partial glycerids of fatty acids | 8 |
| Cetylic alcohol | 0.5 |
| Decylester of oleic acid | 8 |
| Vaseline oil | 4 |
| Karite oil | 16 |
| Polyglycolic ether of saturated fatty alcohol | 4 |

-continued

| Tinted cream in the form of an oil-in-water emulsion | |
|---|---|
| Magnesium and aluminum silicate | 0.7 |
| Polyethylene powder (Polymist B6, ALLIED CHEMICALS Co.) | 4 |
| Iron oxides | 2.2 |
| BHA + BHT | 0.08 |
| Water + preserving agent QSP | 100% by weight |

EXAMPLE 8

| Foundation in the form of a water-in-oil emulsion | |
|---|---|
| Fatty phase: | |
| Paraffin oil | 10 |
| Karite oil | 10 |
| Purcellin oil | 4 |
| Perhydrosqualene | 6 |
| Ozokerite | 2 |
| Magnesium lanolate | 5 |
| Lanolin alcohol | 3 |
| Iron oxides | 3 |
| Titanium dioxide | 4 |
| Polyethylene powder | 10 |
| Fragrance | 0.4 |
| BHA + BHT | 0.01 |
| Water + preserving agent QSP | 100% by weight |

EXAMPLE 9

| Sun-screen cream | |
|---|---|
| Fatty phase: | |
| Vaseline oil | 34 |
| Karite oil | 12 |
| Beeswax | 3 |
| Magnesium lanolate | 2.4 |
| Lanolin alcohol | 0.6 |
| Polyethylene powder | 10 |
| BHA + BHT | 0.01 |
| Solar filter "EUSOLEX 6300" (MERCK Co.) | 3.5 |
| Fragrance | 1 |
| Water + preserving agent QSP | 100% by weight |

EXAMPLE 10

| Body skin milk | |
|---|---|
| Fatty phase: | |
| Karite oil | 3 |
| Vaseline oil | 8 |
| Glycerol stearate | 2 |
| Tween 60 (sorbitan monostearate at 20 moles of ethylene oxide) | 1 |
| Stearic acid | 1.4 |
| Triethanolamine | 0.7 |
| Carbopol 940 (neutralized by triethanolamine) | 0.2 |
| BHA + BHT | 0.01 |
| Fragrance | 1 |
| Water + preserving agent QSP | 100% by weight |

EXAMPLE 11

| Lip care stick | |
|---|---|
| Fatty phase | Grams |
| Microcristalline wax | 10 |
| Candelilla wax | 5 |
| Lanolin | 76.9 |
| Liquid lanolin | 1.6 |
| Karite oil | 12 |
| Thick mineral oil | 8 |

-continued

| Lip care stick | |
|---|---|
| Fatty phase | Grams |
| Cetyl ricinoleate | 20 |
| Vitamin F (essential fatty acids) | 2 |
| Antioxidant | 0.1 |

EXAMPLE 12

| Lipstick, in which the white body has the following composition: | |
|---|---|
| Fatty phase | Grams |
| Microcrystalline wax | 15 |
| Vinyl polylaurate | 10 |
| Docosanoyloxy - 1 (ethyl-2) hexyloxy - 3 propanol | 10 |
| Ricin oil | 25 |
| Cetylic alcohol | 2.5 |
| Triglycerids of capric/caprylic acids | 3.3 |
| Karite oil | 10 |
| Acetylated lanolin | 5 |
| Arachidyl propionate | 5 |
| Sesame oil | 10 |
| Acetoglycerids | 4 |
| Antioxidant | 0.2 |

EXAMPLE 13

| Anhydrous ointment | |
|---|---|
| Fatty phase | Grams |
| Karite oil | 60 |
| Sesame oil | 20 |
| Vaseline | 15 |
| Soybean lecithin | 4.8 |
| BHA | 0.1 |
| BHT | 0.1 |

EXAMPLE 14

| Anhydrous make-up removing gel | |
|---|---|
| Fatty phase | Grams |
| Ropy vaseline | 50 |
| Isopropyl palmitate | 20 |
| Paraffin oil | 20 |
| Karite oil + antioxidant | 9.8 |
| (BHA + BHT) | 0.2 |

EXAMPLE 15

| Face and body care oil | |
|---|---|
| Fatty phase | Grams |
| Karite oil | 2 |
| Soybean oil | 32 |
| Sunflower oil | 31.8 |
| Peanut oil | 32 |
| BHA + BHT | 0.2 |
| Vitamin F (essential fatty acids) | 0.4 |

EXAMPLE 16

| Sun-screen oil | |
|---|---|
| Fatty phase | Grams |
| Karite oil | 1 |
| Colza oil QSP | 100 |
| 2-ethyl hexyl paramethoxy cinnamate sold under the name "PARSOL MEX" by GIVAUDAN Company | 2.5 |

-continued

| Sun-screen oil | |
|---|---|
| Fatty phase | Grams |
| BHA | 0.025 |
| BHT | 0.025 |
| Coloring agent QS | |
| Fragrance QS | |

We claim:

1. In a cosmetic preparation for face and body care containing a fatty phase, the improvement consisting of, as said fatty phase, karite oil having the following characteristics: palmitic acid ($C_{16}$), 3–5 percent; stearic acid ($C_{18}$), 22–30 percent; oleic acid ($C_{18:1}$), 55–65 percent; linoleic acid ($C_{18:2}$), 0.5–1.5 percent; and arachidic acid ($C_{20}$), 0.5–1.5 percent, said percentages being based on the total weight of fatty acid present in said karite oil, a viscosity of 100–300 centipoises, a melting point of 5.1°–5.4° C., a crystallization temperature of 2.9°–3° C. and an unsaponifiable content of 1.2–1.5 percent.

2. The cosmetic preparation of claim 1 wherein said karite oil has the following fatty acid ratios:

$$[(C_{16}+C_{18})/C_{18:1}] = 0.518 \pm 0.01 \text{ and}$$

$$(C_{16}/C_{18:1}) = 0.064 \pm 0.003.$$

3. The cosmetic preparation of claim 1 wherein said karite oil is present in an amount of 1 to 80 percent by weight based on the total weight of said preparation.

4. In a cosmetic preparation for face and body care in the form of an oil-in-water emulsion or a water-in-oil emulsion, said emulsion comprising a fatty phase, a water phase and an emulsifier, the improvement consisting of, as said fatty phase, karite oil having the following characteristics: palmitic acid ($C_{16}$), 3–5 percent; stearic acid ($C_{18}$), 22–30 percent; oleic acid ($C_{18:1}$), 55–65 percent; linoleic acid ($C_{18:2}$), 0.5–1.5 percent; and and arachidic acid ($C_{20}$), 0.5–1.5 percent, said percentages being based on the total weight of fatty acid present in said karite oil; a viscosity of 100–300 centipoises, a melting point of 5.1°–5.4° C., a crystallization temperature of 2.9°–3° C. and an unsaponifiable content of 1.2–1.5 percent.

5. The cosmetic preparation of claim 4 wherein said fatty phase is present in an amount of 4 to 60 weight percent, said water phase is present in an amount of 30 to 90 weight percent and said emulsifier is present in an amount of 1 to 20 weight percent.

6. The cosmetic preparation of claim 5 wherein said fatty phase comprises 2 to 30 weight percent karite oil based on the total weight of said preparation.

7. The cosmetic preparation of claim 5 which also includes an essential fatty acid selected from the group consisting of linoleic acid, α-linolenic acid, γ-linolenic acid and arachidonic acid.

8. The cosmetic preparation of claim 5 which also includes as an essential fatty acid, Vitamin F present in an amount of 0.2 to 20 weight percent based on the total weight of karite oil in said preparation.

9. The cosmetic preparation of claim 7 wherein said essential fatty acid is present in an amount of 0.2 to 20 weight percent based on the weight of karite oil in said preparation.

10. The cosmetic preparation of claim 4 which also includes an antioxidant selected from the group consisting of butylhydroxyanisole, butylhydroxytoluene and a mixture thereof, said antioxidant being present in an amount of 0.002 to 0.2 percent by weight based on the total weight of said preparation.

* * * * *